(12) United States Patent
Shimizu et al.

(10) Patent No.: US 8,377,627 B2
(45) Date of Patent: Feb. 19, 2013

(54) COMPOUND AND RADIATION-SENSITIVE COMPOSITION

(75) Inventors: Daisuke Shimizu, Tokyo (JP); Ken Maruyama, Tokyo (JP); Toshiyuki Kai, Tokyo (JP); Tsutomu Shimokawa, Tokyo (JP)

(73) Assignee: JSR Corporation, Tokyo (JP)

( * ) Notice: Subject to any disclaimer, the term of this patent is extended or adjusted under 35 U.S.C. 154(b) by 136 days.

(21) Appl. No.: 12/673,167

(22) PCT Filed: Jul. 30, 2008

(86) PCT No.: PCT/JP2008/063653
§ 371 (c)(1),
(2), (4) Date: Feb. 9, 2011

(87) PCT Pub. No.: WO2009/022540
PCT Pub. Date: Feb. 19, 2009

(65) Prior Publication Data
US 2011/0117489 A1   May 19, 2011

(30) Foreign Application Priority Data
Aug. 13, 2007   (JP) .................................. 2007-210715

(51) Int. Cl.
G03F 7/004 (2006.01)
C07C 69/96 (2006.01)
C07C 69/76 (2006.01)
C07C 39/12 (2006.01)

(52) U.S. Cl. ...... 430/270.1; 430/914; 430/919; 430/921; 568/632; 568/719; 568/720; 568/731; 568/744; 560/59; 558/269

(58) Field of Classification Search ............... 430/270.1, 430/326, 914, 919, 921; 568/720, 721, 744, 568/722, 719, 723, 729, 731, 732, 733; 562/405, 562/480, 488, 489, 491
See application file for complete search history.

(56) References Cited

U.S. PATENT DOCUMENTS

| | | | |
|---|---|---|---|
| 5,702,620 A | 12/1997 | Ohnishi et al. | |
| 5,744,537 A | 4/1998 | Brunsvold et al. | |
| 6,117,617 A | 9/2000 | Kanayama et al. | |
| 6,177,231 B1 | 1/2001 | Ishii et al. | |
| 6,395,447 B1 | 5/2002 | Ishii et al. | |
| 6,576,400 B1 | 6/2003 | Tamura | |
| 7,705,189 B2 * | 4/2010 | Nishikubo et al. | 568/632 |
| 8,173,351 B2 * | 5/2012 | Shimizu et al. | 430/270.1 |
| 2007/0123736 A1 | 5/2007 | Nishikubo et al. | |
| 2009/0035691 A1 | 2/2009 | Shiono et al. | |

FOREIGN PATENT DOCUMENTS

| | | |
|---|---|---|
| EP | 0159428 | 10/1985 |
| EP | 1806619 | 7/2007 |
| JP | 6-12452 B2 | 5/1984 |
| JP | 5-188598 | 7/1993 |
| JP | 7-134413 | 5/1995 |
| JP | 9-211862 | 8/1997 |
| JP | 9-236919 | 9/1997 |
| JP | 10-282649 | 10/1998 |
| JP | 11-29612 | 2/1999 |
| JP | 11-072916 | 3/1999 |
| JP | 11-143074 | 5/1999 |
| JP | 11-258796 | 9/1999 |
| JP | 11-322656 | 11/1999 |
| JP | 2000-147777 | 5/2000 |
| JP | 2006-235340 | 9/2006 |
| JP | 2006-267996 | 10/2006 |
| JP | 2007-8875 | 1/2007 |
| WO | WO 2005/075398 | 8/2005 |
| WO | WO 2008/038544 | 4/2008 |
| WO | WO 2008/084786 | 7/2008 |

OTHER PUBLICATIONS

Machine translation of JP-2007-8875 (no date).*
Heidi Cao et al., "Sources of Line Width Roughness for EUV Resists", Proceedings of SPIE vol. 5376, pp. 757-764 (SPIE, Bellingham, WA, 2004).
Kadota et al., "Amorphous Molecular Materials: Development of a Novel Positive Electron-beam Molecular Resist", Journal of Photopolymer Science and Technology, vol. 12, No. 2 (1999) pp. 375-376.
International Search Report for corresponding International Application No. PCT/JP2008/063653, Sep. 16, 2008.
International Preliminary Report on Patentability with Written Opinion of the International Searching Authority for corresponding International Application No. PCT/JP2008/063653, Mar. 9, 2010.

* cited by examiner

*Primary Examiner* — Amanda C. Walke
(74) *Attorney, Agent, or Firm* — Ditthavong Mori & Steiner, P.C.

(57) ABSTRACT

A compound shown by the following formula (1).

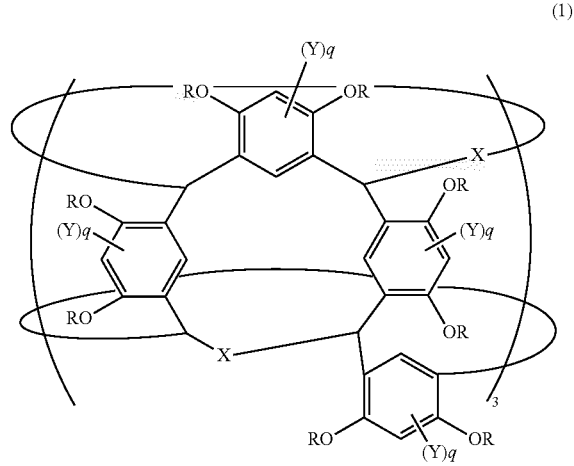

6 Claims, No Drawings

COMPOUND AND RADIATION-SENSITIVE COMPOSITION

TECHNICAL FIELD

The present invention relates to a compound and a radiation-sensitive composition. More particularly, the present invention relates to a compound used as a material for a positive-tone radiation-sensitive composition capable of forming a fine pattern using electron beams (hereinafter referred to from time to time as "EB") or extreme ultraviolet rays (hereinafter referred to from time to time as "EUV"), and to the radiation-sensitive composition.

BACKGROUND ART

In the field of microfabrication represented by fabrication of integrated circuit devices by a lithography process, design rules have become more and more minute in order to achieve higher integration. Development of a lithography process enabling microfabrication in a stable manner has been actively pursued.

However, it is difficult to precisely form a fine pattern by a lithography process using KrF or ArF excimer laser beams. For this reason, in order to achieve microfabrication, a lithography process using electron beams in place of KrF or ArF excimer laser beams has been proposed in recent years.

There have been a number of reports disclosing a resist material used for a lithography process using electron beams. Examples of such reports include (1) a positive-tone resist containing a methacryl-main-chain-cut-polymer such as polymethyl methacrylate (PMMA) (for example, refer to Patent Documents 1 and 2), (2) a chemically-amplified positive-tone resist containing a polyhydroxystyrene resin partially protected by an acid-labile group (resin for KrF excimer laser beams), a novolak resin (resin for i-lines), and an acid generator (for example, refer to Non-patent Document 1), (3) a positive-tone and negative-tone resist containing an organic low molecular weight molecule having thin film forming capabilities (amorphous properties) such as calixarene and fullerene (for example, refer to Patent Documents 3 to 11) or a resist using a polyhydric phenol compound (for example, refer to Patent Documents 12 and 13). In addition, a chemically-amplified resist containing 1,3,5-tris[4-(2-t-butoxycarbonyloxy)phenyl]benzene as an organic low molecular weight compound having thin film forming capabilities other than calixarene and fullerene has also been proposed (for example, refer to Non-patent Document 2).

Patent Document 1: JP-A-2000-147777
Patent Document 2: JP-A-11-29612
Patent Document 3: JP-A-11-322656
Patent Document 4: JP-A-11-72916
Patent Document 5: JP-A-9-236919
Patent Document 6: WO 2005/075398
Patent Document 7: JP-A-7-134413
Patent Document 8: JP-A-9-211862
Patent Document 9: JP-A-10-282649
Patent Document 10: JP-A-11-143074
Patent Document 11: JP-A-11-258796
Patent Document 12: JP-A-2006-267996
Patent Document 13: JP-A-2006-235340
Non-patent Document 1: Proc. SPIE. VOL. 5376, 757-764 (2004)
Non-patent Document 2: J. Photo Sci. & Tech. VOL. 12, No. 2, 375-376 (1999)

However, among the above-mentioned electron beam resist materials, the positive-tone resist (1) has problems in etching resistance and sensitivity. It is difficult to use this resist in practice. In order to improve sensitivity, a resist using poly-t-butyl α-chloromethylstyrene or a resin having atoms that makes the resin easily cut by electron beams such as N, O, and S introduced into the terminals have been proposed (Patent Documents 1 and 2). Although a certain degree of improvement in the sensitivity can be seen, the sensitivity and etching resistance of these resins still remain at a level unusable in practice. The chemically-amplified positive-tone resist (2) described in Non-patent Document 1 has high sensitivity. But, due to the use of a resin, the resist has a problem of film surface roughness (hereinafter referred to from time to time as "nano-edge roughness" or "roughness") when forming minute patterns. The resists (3) using calixarene have excellent etching resistance (for example, Patent Documents 3 to 5). However, these resists have very strong interaction between the molecules due to their structure. Their solubility in a developer is poor and it is difficult to obtain satisfactory patterns. The nano-edge roughness performance of the compound using calixarene derivatives described in Patent Document 6 is not clear.

Even though the resists using fullerene described in Patent Documents 7 to 11 have excellent etching resistance, their coatability and sensitivity are not at a usable level in practice. In addition, the chemically-amplified resist containing 1,3,5-tris[4-(2-t-butoxycarbonyloxy)phenyl]benzene as an organic low molecular weight compound having thin film forming capabilities other than calixarene and fullerene disclosed in Non-patent Document is not sufficient and still needs to be improved in coatability, adhesion to a substrate, and sensitivity in order to become usable in practice. The resists using a polyhydric phenol compound (for example, Patent Documents 12 and 13) exhibit excellent resolution, but their sensitivity is still needs to be improved in order to be used in practice.

The radiation-sensitive compositions disclosed in the Patent Documents 1 to 13 and Non-patent Document 1 and 2 above prior art documents still need to be improved as mentioned above. In addition, none of these compositions can produce a chemically-amplified positive-tone resist film effectively responsive to electron beams or extreme ultraviolet rays, exhibiting excellent resolution, sensitivity, and pattern shape-forming capabilities, and capable of precisely and stably forming fine patterns.

The present invention has been achieved in view of these prior art problems and has an object of providing a compound used as a material for a radiation-sensitive composition capable of forming a chemically-amplified positive-tone resist film which effectively responds to electron beams or extreme ultraviolet rays, exhibits excellent resolution, sensitivity, and pattern shape-forming capabilities, and is capable of precisely and stably forming fine patterns, and a radiation-sensitive composition including the compound.

DISCLOSURE OF THE INVENTION

As a result of extensive studies in order to achieve the above object, the inventors of the present invention have found that the above object can be achieved by a compound having a specific structure, and by a radiation-sensitive composition including this compound and a radiation-sensitive acid generator. The finding has led to the completion of the present invention.

According to the present invention, the following compound and radiation-sensitive composition are provided.

[1] A compound shown by the following formula (1),

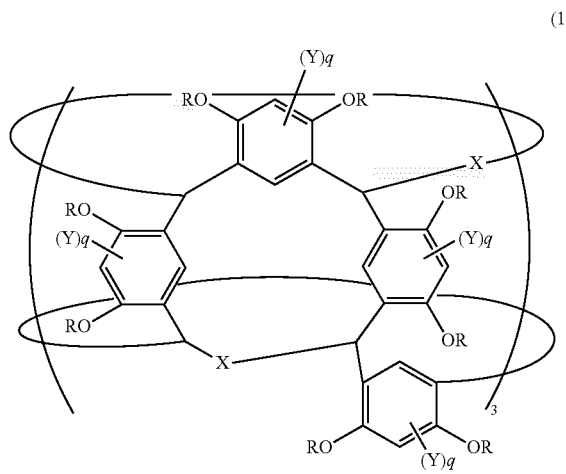

(1)

wherein R individually represent a hydrogen atom or a substituted or unsubstituted monovalent acid-labile group having a chain-like structure, provided that at least one R is a substituted or unsubstituted monovalent acid-labile group having a chain-like structure, and at least one R is a hydrogen atom, X individually represent a substituted or unsubstituted alkylene group having 1 to 8 carbon atoms, Y individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxy group having 1 to 10 carbon atoms, or a substituted or unsubstituted phenoxy group, and q individually represent 0 or 1.

[2] The compound according to [1], wherein the acid-labile group is a group shown by the following formula (2-1) or (2-2),

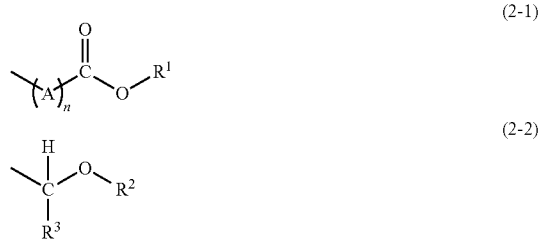

(2-1)

(2-2)

wherein A represents a methylene group or a divalent alkylene group having 2 to 11 carbon atoms which may be unsubstituted or substituted by a substituent which may include a hetero atom, n represents an integer from 0 to 3, $R^1$ represents a linear or branched alkyl group having 1 to 40 carbon atoms which may be unsubstituted or substituted by a substituent which may include a hetero atom, $R^2$ represents an alkyl group having 1 to 40 carbon atoms which may be unsubstituted or substituted by a substituent which may include a hetero atom, and $R^3$ represents a hydrogen atom or an alkylene group having 1 to 5 carbon atoms.

[3] The compound according to [2], wherein the group shown by the formula (2-1) is a group shown by the following formula (3-1) or (3-2), and the group shown by the formula (2-2) is a group shown by the following formula (4-1), (4-2), (4-3), or (4-4).

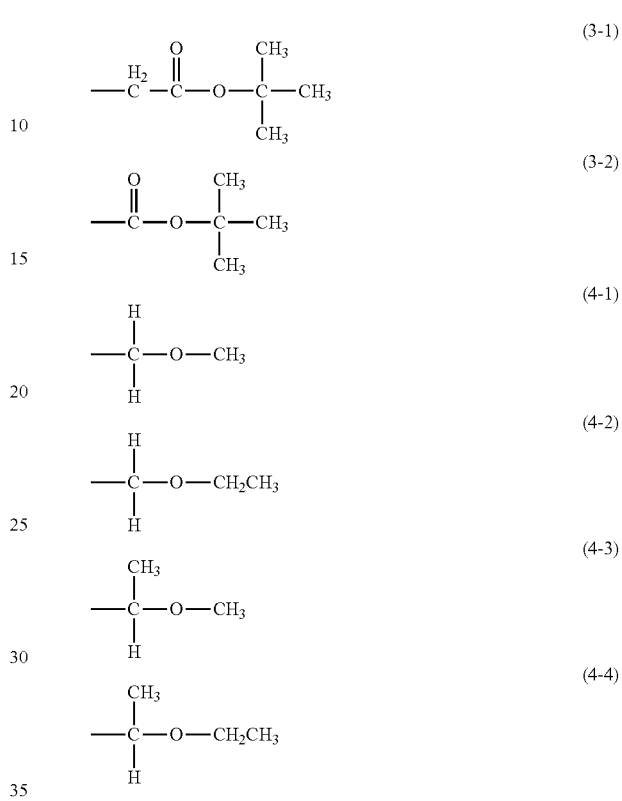

[4] A radiation-sensitive composition including (a) a compound according to any one of [1] to [3], and (b) a radiation-sensitive acid generator which generates an acid upon irradiation.

[5] The radiation-sensitive composition according to [4], wherein the radiation-sensitive acid generator (b) is at least one compound selected from the group consisting of an onium salt, a diazomethane compound, and a sulfonimide compound.

[6] The radiation-sensitive composition according to [4] or [5], further including (c) an acid diffusion controller.

Due to the structure shown by the above formula (1), the compound of the present invention can form a chemically-amplified positive-tone resist film which effectively responds to electron beams or extreme ultraviolet rays, exhibits excellent resolution, sensitivity, and pattern shape-forming capabilities, and is capable of precisely and stably forming fine patterns, when used as a material of a radiation-sensitive composition.

Due to inclusion of the compound of the present invention, the radiation-sensitive composition of the present invention can form a chemically-amplified positive-tone resist film which effectively responds to electron beams or extreme ultraviolet rays, exhibits excellent resolution, sensitivity, and pattern forming capabilities, and is capable of forming high precision minute patterns in a stable manner.

BEST MODE FOR CARRYING OUT THE INVENTION

Preferred embodiments of the present invention are described below. Note that the present invention is not limited to the following embodiments. Various modifications and improvements may be made in the following embodiments within the scope of the present invention based on the knowledge of a person skilled in the art.

[1] Compound

One embodiment of the compound of the present invention is shown by the following formula (1) (hereinafter may be referred to from time to time as "compound (a)"). The compound (a) is an acid-labile group containing compound which includes or is modified by a substituted or unsubstituted monovalent acid-labile group having a chain structure. Therefore, the acid-labile group in the compound (a) dissociates by the action of an acid and the compound becomes soluble in alkali after dissociation of the acid-labile group. Due to the properties of the compound (a) to become alkali soluble, exposed parts of the resist film formed from the radiation-sensitive composition containing the compound (a) can be easily removed by an alkaline developer. As a result, not only high precision fine patterns can be stably formed, but also the formed resist patterns have a good shape. In addition, due to the possession of a phenolic hydroxyl group of the compound (a), the formed resist film has high adhesion with the substrate, whereby the resist pattern is prevented from collapsing and excellent precision can be ensured.

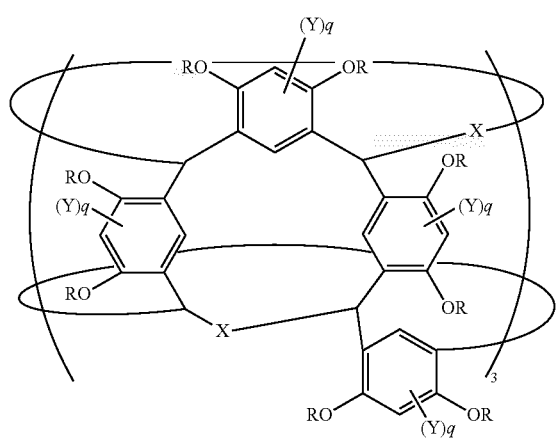

(1)

wherein R individually represent a hydrogen atom or a substituted or unsubstituted monovalent acid-labile group having a chain-like structure, provided that at least one R is a substituted or unsubstituted monovalent acid-labile group having a chain-like structure and at least one R is a hydrogen atom, X individually represent a substituted or unsubstituted alkylene group having 1 to 8 carbon atoms; Y individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxy group having 1 to 10 carbon atoms, or a substituted or unsubstituted phenoxy group; and q individually represent 0 or 1.

The formula (1) may alternatively shown by the following formula (1-1), (1-1)

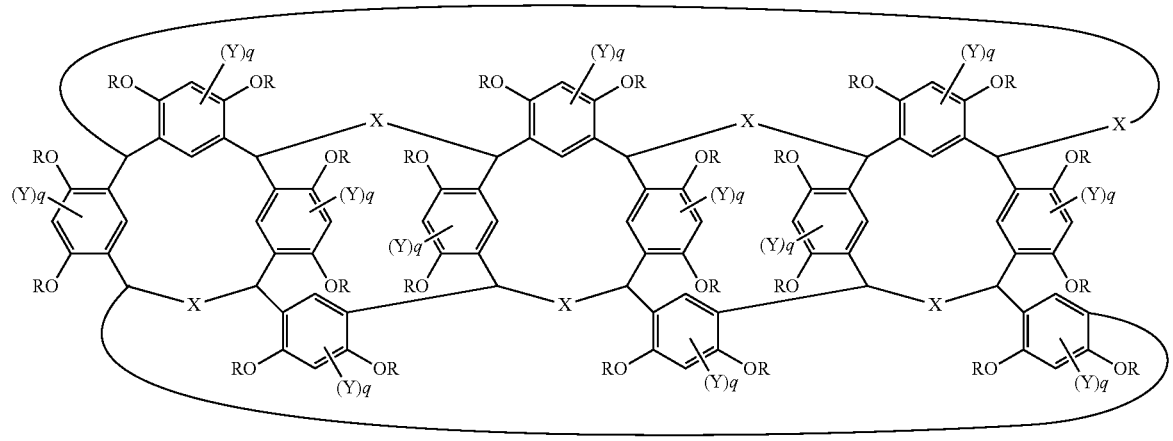

wherein R individually represent a hydrogen atom or a substituted or unsubstituted monovalent acid-labile group having a chain-like structure, provided that at least one R is a substituted or unsubstituted monovalent acid-labile group having a chain-like structure and at least one R is a hydrogen atom. X individually represent a substituted or unsubstituted alkylene group having 1 to 8 carbon atoms; Y individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxy group having 1 to 10 carbon atoms, or a substituted or unsubstituted phenoxy group; and q individually represent 0 or 1.

As examples of the substituents for the substituted alkyl group having 1 to 10 carbon atoms shown by Y in the formula (1), a methyl group, an ethyl group, a propyl group, and a butyl group can be given. Of these, a propyl group and a butyl group are preferable in order to obtain the compound of the embodiment in high yield.

Among the compounds shown by the formula (1), a compound shown by the following formula (2) is preferable. Specifically, it is preferable that X be a propylene group and q be 0 in the formula (1). Among the compounds shown by the formula (1), a compound shown by the following formula (2) can be produced in high yield.

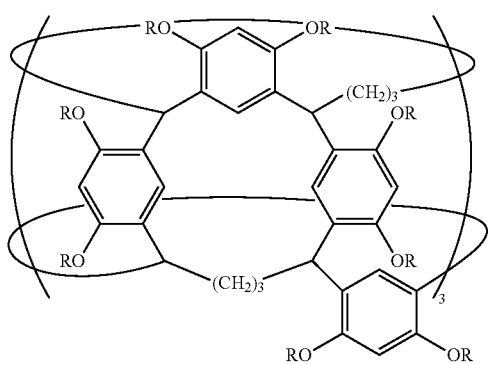

(2)

wherein R individually represent a hydrogen atom or a substituted or unsubstituted monovalent acid-labile group having a chain-like structure, provided that at least one R is a substituted or unsubstituted monovalent acid-labile group having a chain-like structure and at least one R is a hydrogen atom,

[1-1] Acid-Labile Group

R in the above formula (1) individually represent a hydrogen atom or a substituted or unsubstituted monovalent acid-labile group having a chain-like structure, provided that at least one R is a substituted or unsubstituted monovalent acid-labile group having a chain-like structure and at least one R is a hydrogen atom.

If all R in the formula (1) are acid-labile groups, a resist film formed from the radiation-sensitive composition containing the compound of the embodiment produces a resist pattern having impaired nanoedge roughness when patterning is performed, resulting in a film with a roughened surface.

Among all R in the compound shown by the formula (1), the proportion of the acid-labile groups is preferably 10 to 90 mol %, and more preferably 20 to 80 mol %. If the proportion of the acid-labile groups is in the above range, the radiation-sensitive composition containing the compound of the embodiment has an advantage of exhibiting promoted film-forming capability when applied to a substrate due to good action of the phenolic hydroxyl group on the substrate. In addition, if the phenolic hydroxyl group favorably acts on a substrate, resist pattern collapse can be suppressed, resulting in improved resist pattern resolution. The proportion of the acid-labile group in the compound shown by the formula (1) is calculated based on the results of $^1$H-NMR analysis.

The acid-labile group is either substituted or unsubstituted and has a monovalent chain-like structure. The term "monovalent acid-labile group having a chain-like structure" indicates a monovalent acid-labile group having no cyclic structure in the molecule, for example, a linear or branched monovalent acid-labile group. Although there are no particular limitations to the structure of the acid-labile group insofar as the group has a substituted or unsubstituted monovalent chain-like structure and is dissociable by the action of an acid, the groups shown by the following formula (2-1) or (2-2) are preferable. Since R in the formula (1) "individually" represent the defined groups, when two or more acid-labile groups are present in the formula (1), all R may be the group shown by the following formula (2-1) or the group shown by the following formula (2-2), or both the groups shown by the following formula (2-1) and the group shown by the following formula (2-2) may be present.

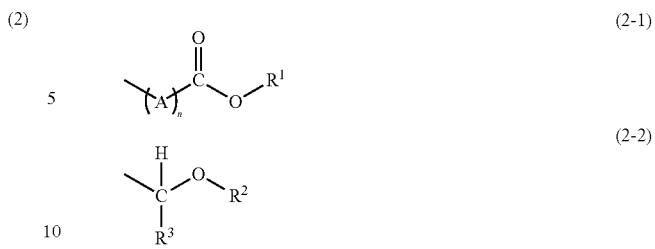

wherein, in the above formula (2-1), A represents a methylene group or a divalent alkylene group having 2 to 11 carbon atoms which may be unsubstituted or substituted by a substituent which may include a hetero atom, n is an integer from 0 to 3, and $R^1$ represents a linear or branched alkyl group having 1 to 40 carbon atoms which may be unsubstituted or substituted by a substituent which may include a hetero atom, and, in the formula (2-2), $R^2$ represents an alkyl group having 1 to 40 carbon atoms which may be unsubstituted or substituted by a substituent which may include a hetero atom, and $R^3$ represents a hydrogen atom or an alkylene group having 1 to 5 carbon atoms.

A in the above formula (2-1) is preferably an alkyl group having 1 to 4 carbon atoms, and more preferably an alkyl group having 1 or 2 carbon atoms.

n in the above formula (2-1) is preferably 0 to 2, and more preferably 0 to 1.

$R^1$ in the above formula (2-1) is preferably an alkyl group having 1 to 40 carbon atoms, and more preferably an alkyl group having 1 or 20 carbon atoms.

Among the groups shown by the formula (2-1), a group shown by the formula (3-1) or a group shown by the formula (3-2) is preferable. A compound having a group shown by the formula (3-1) and a compound having a group shown by the formula (3-2) have an advantage of easy industrial availability. When two or more groups shown by the formula (2-1) are present, all the groups shown by the formula (2-1) may be the same group or each of such groups may be different from the others.

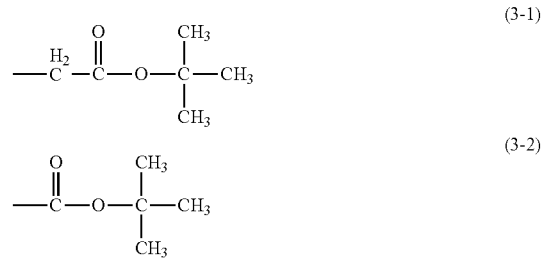

$R^2$ in the above formula (2-2) is preferably an alkyl group having 1 to 40 carbon atoms, and more preferably an alkyl group having 1 or 20 carbon atoms.

Among the compounds having a group shown by the formula (2-2), those having a hydrogen atom or an alkyl group having 1 to 5 carbon atoms for $R^3$ in the formula (2-2) are preferable due to easy industrial availability, and those having a hydrogen atom or an alkyl group having 1 or 2 carbon atoms for $R^3$ are more preferable.

Among the groups shown by the above formula (2-2), the groups shown by the formula (4-1), (4-2), (4-3), or (4-4) are preferable. A compound having the group shown by the above formula (4-1), (4-2), (4-3), or (4-4) has an advantage of easy industrial availability. When two or more groups shown by the formula (2-2) are present, all the groups shown by the formula (2-2) may be the same group or each of such groups may be different from the others.

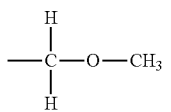
(4-1)

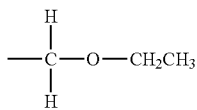
(4-2)

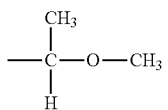
(4-3)

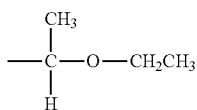
(4-4)

[1-2] Method for Producing the Compound Shown by the Formula (1)

The compound of the embodiment can be obtained by reacting a compound shown by the following formula (1-2) and a compound shown by the following formula (1-3) by a condensation reaction to produce a precursor compound shown by the following formula (1-4), and introducing at least one substituted or unsubstituted acid-labile group having a chain-like structure into the precursor compound shown by the following formula (1-4),

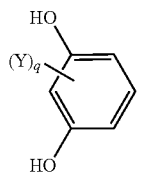
(1-2)

wherein Y represents a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxy group having 1 to 10 carbon atoms, or a substituted or unsubstituted phenoxy group, and q represent 0 or 1,

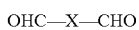
OHC—X—CHO (1-3)

wherein X represents a substituted or unsubstituted alkylene group having 1 to 8 carbon atoms,

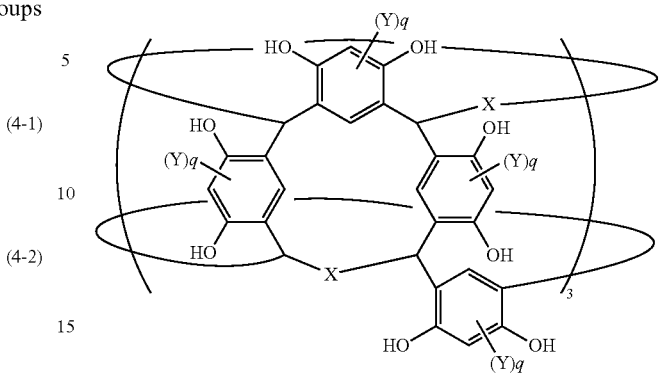
(1-4)

wherein X individually represent a substituted or unsubstituted alkylene group having 1 to 8 carbon atoms; Y individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxy group having 1 to 10 carbon atoms, or a substituted or unsubstituted phenoxy group; and q individually represent 0 or 1.

There are no particular limitations to the conditions (method) of the condensation reaction. A general method of reacting in the presence of a catalyst such as an acid catalyst at 60 to 90° C. for 12 to 50 hours can be given, for example.

There are no particular limitations to the conditions (method) of introducing the acid-labile group. A general method such as a method of reacting the compound having a monovalent acid-labile group which has a substituted or unsubstituted chain-like structure in the presence of an acid or a base in a solvent at −20 to 100° C. for 1 to 20 hours can be given.

The amount of the acid-labile group to be introduced, that is, the proportion of the acid-labile group in all R of the compound shown by the formula (1), may be adjusted by controlling the total amount of the compound having the group shown by the formula (2-1) and the compound having the group shown by the formula (2-2) added to the precursor shown by the formula (1-4).

In producing the compound shown by the above formula (2), a compound shown by the following formula (5) and a compound shown by the following formula (6) are reacted at 60 to 90° C. for 12 to 50 hours in a solvent in the presence of a catalyst to effect a dehydration condensation reaction to produce a precursor (a precursor having q=0 in the formula (1-4), hereinafter referred to from time to time as "precursor (1-4)"). As a catalyst, an acid catalyst can be given for example.

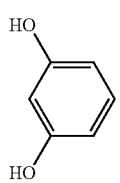
(5)

OHC—(CH$_2$)$_3$—CHO (6)

The precursor (1-4) is then reacted with, for example, a compound having the group shown by the formula (2-1), a compound having the group shown by the formula (2-2), or a mixture of these compounds at −20 to 100° C. for 1 to 20 hours in a solvent in the presence of an acid or a base to obtain the compound shown by the formula (2).

Although there are no particular limitations to the mixing ratio (molar ratio) of the compound shown by the above formula (5) (hereinafter referred to from time to time as "compound (5)") and the compound shown by the above formula (6) (hereinafter referred to from time to time as "compound (6)"), the amount of the compound (5) per one mol of the compound (6) is preferably 1.00 to 8.00 mol, more preferably 2.00 to 6.00 mol, and particularly preferably 3.00 to 5.00 mol from the viewpoint of producing the compound of the embodiment in high yield. If the mixing ratio of the compound (5) is less than 1.00 mol, the yield of the compound of the embodiment may decrease. If more than 8.00 mol, the yield of the compound of the embodiment may also decrease.

Although the concentration of the substrate (concentration of the total of the compound (5) and compound (6) in the reaction solution) is not particularly limited, a concentration of 2 mol/l or more is preferable, a concentration of 4 mol/l or more is more preferable, and a concentration of 4 to 10 mol/l is particularly preferable in order to produce the compound of the embodiment in high yield. If the substrate concentration is less than 2 mol/l, the yield of the resulting compound of the embodiment may decrease.

Although there are no particular limitations to the mixing ratio (mol ratio) of the above precursor (1-4) to the compound having the group shown by the formula (2-1) or the compound having the group shown by the formula (2-2) (the total amount of these compounds when a mixture of these is used), the amount of the compound having the group shown by the formula (2-1) or the compound having the group shown by the formula (2-2) (the total amount of these compounds when a mixture of these is used) per one mol of the precursor (1-4) is preferably one mol or more, more preferably 5 to 40 mol, and particularly preferably 5 to 20 mol in order to ensure a high yield of the compound of the embodiment. If the amount of the compound having the group shown by the formula (2-1) or the compound having the group shown by the formula (2-2) (the total amount of these compounds when a mixture of these is used) is one mol or more, the target compound of the embodiment can be efficiently synthesized in high yield. If less than one mol, the yield of the target compound (the compound of the embodiment) may decrease.

[2] Radiation-Sensitive Composition

The radiation-sensitive composition in one embodiment of the present invention includes (a) the compound of the present invention and (b) a radiation-sensitive acid generator which generates an acid by being irradiated. Inclusion of the compound (a) enables formation of a resist film of which exposed parts can be removed with ease by alkali development after exposure to produce high precision fine patterns in a stable manner. In addition, since the compound (a) of the radiation-sensitive composition has a phenolic hydroxyl group which favorably acts on a substrate when applied thereon, a resist film with excellent adhesion to a substrate can be formed.

The compound (a) contained in the radiation-sensitive composition of the present embodiment further includes an acid-labile group. Therefore, exposed parts of the resist film formed from the radiation-sensitive composition of this embodiment becomes easily removable by an alkaline developer as in a general chemically-amplified resist film (as described in above-mentioned prior art documents, for example). For this reason, the resist film has excellent sensitivity. In addition, if an acid-labile group is partly introduced, the compound (a) favorably reacts with a developer due to phenolic hydroxyl groups remaining in the compound (a), resulting in an excellent pattern shape. The composition of the embodiment thus can form a resist film which effectively responds to electron beams or extreme ultraviolet rays, exhibits high resolution, excels in etching resistance and sensitivity, and can form high precision minute patterns in a stable manner, when used in a lithography process.

[2-1] Radiation-Sensitive Acid Generator

The radiation-sensitive acid generator (b) is a component which produces an acid when the radiation-sensitive composition of the present invention is irradiated with electron beams or radioactive rays in a lithography process. An acid-labile group in the above-described compound (a) is dissociated by the action of the generated acid.

As the radiation-sensitive acid generator (b), at least one compound selected from the group consisting of, for example, an onium salt, a diazomethane compound, and a sulfonimide compound is preferable due to excellent acid generating efficiency and heat resistance. These substances may be used either individually or in a combination of two or more.

As examples of the onium salt, an iodonium salt, sulfonium salt, phosphonium salt, diazonium salt, and pyridinium salt can be given. As specific examples of the onium salt, triphenylsulfonium trifluoromethanesulfonate, triphenylsulfonium nonafluoro-n-butanesulfonate, triphenylsulfonium benzenesulfonate, triphenylsulfonium 10-camphorsulfonate, triphenylsulfonium n-octanesulfonate, triphenylsulfonium 4-trifluoromethylbenzensulfonate, triphenylsulfonium naphthalenesulfonate, triphenylsulfonium perfluorobenzenesulfonate, triphenylsulfonium 1,1,2,2-tetrafluoro-2-(tetracyclo[4.4.0.1$^{2,5}$.1$^{7,10}$]dodecan-8-yl)ethanesulfonate, triphenylsulfonium 1,1-difluoro-2-(bicyclo[2.2.1]heptane-2-yl)ethanesulfonate;

(4-t-butoxyphenyl)diphenylsulfonium trifluoromethanesulfonate, (4-t-butoxyphenyl)diphenylsulfonium nonafluoro-n-butanesulfonate, (4-t-butoxyphenyl)diphenylsulfonium perfluoro-n-octanesulfonate, (4-t-butoxyphenyl) diphenylsulfonium 10-camphorsulfonate, (4-hydroxyphenyl)diphenylsulfonium trifluoromethanesulfonate, (4-hydroxyphenyl)diphenylsulfonium nonafluoro-n-butanesulfonate, (4-hydroxyphenyl)diphenylsulfonium perfluoro-n-octanesulfonate, (4-hydroxyphenyl) diphenylsulfonium 10-camphorsulfonate, (4-hydroxyphenyl)diphenylsulfonium n-octanesulfonate, tris(4-methoxyphenyl)sulfonium trifluoromethanesulfonate, tris(4-methoxyphenyl)sulfonium nonafluoro-n-butanesulfonate, tris(4-methoxyphenyl)sulfonium perfluoro-n-octanesulfonate, tris(4-methoxyphenyl)sulfonium 10-camphorsulfonate, (4-fluorophenyl)diphenylsulfonium trifluoromethanesulfonate, (4-fluorophenyl)diphenylsulfonium nonafluoro-n-butanesulfonate, (4-fluorophenyl)diphenylsulfonium 10-camphorsulfonate; tris(4-fluorophenyl)sulfonium trifluoromethanesulfonate, tris(4-fluorophenyl)sulfonium nonafluoro-n-butanesulfonate, tris(4-fluorophenyl)sulfonium 10-camphorsulfonate, tris(4-fluorophenyl)sulfonium p-toluenesulfonate, tris(4-trifluoromethylphenyl)sulfonium trifluoromethanesulfonate;

2,4,6-trimethylphenyldiphenylsulfonium trifluoromethanesulfonate, 2,4,6-trimethylphenyldiphenylsulfonium 2,4-difluorobenzenesulfonate, 2,4,6-trimethylphenyldiphenylsulfonium 4-trifluoromethylbenzensulfonate; diphenyliodonium trifluoromethanesulfonate, diphenyliodonium nonafluoro-n-butanesulfonate, diphenyliodonium perfluoro-n-octanesulfonate, diphenyliodonium 10-camphorsulfonate, diphenyliodonium n-octanesulfonate,
bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 10-camphorsulfonate, bis(4-t-butylphenyl)iodonium n-octanesulfonate, (4-methoxyphenyl)phenyliodonium trifluoromethanesulfonate, (4-methoxyphenyl)phenyliodonium nonafluoro-n-butanesulfonate, (4-methoxyphenyl)phenyliodonium perfluoro-n-octanesulfonate,
(4-fluorophenyl)phenyliodonium trifluoromethanesulfonate, (4-fluorophenyl)phenyliodonium nonafluoro-n-butanesulfonate, (4-fluorophenyl)phenyliodonium 10-camphorsulfonate; bis(4-fluorophenyl)iodonium trifluoromethanesulfonate, bis(4-fluorophenyl)iodonium nonafluoro-n-butanesulfonate, bis(4-fluorophenyl)iodonium 10-camphorsulfonate;
bis(4-chlorophenyl)iodonium trifluoromethanesulfonate, bis(4-chlorophenyl)iodonium nonafluoro-n-butanesulfonate, bis(4-chlorophenyl)iodonium perfluoro-n-octanesulfonate, bis(4-chlorophenyl) iodonium-n-dodecylbenzenesulfonate, bis(4-chlorophenyl)iodonium 10-camphorsulfonate, bis(4-chlorophenyl)iodonium n-octanesulfonate, bis(4-chlorophenyl)iodonium 4-trifluoromethylbenzensulfonate, bis(4-chlorophenyl)iodonium perfluorobenzenesulfonate;
bis(4-trifluoromethylphenyl)iodonium trifluoromethanesulfonate, bis(4-trifluoromethylphenyl)iodonium nonafluoro-n-butanesulfonate, bis(4-trifluoromethylphenyl)iodonium perfluoro-n-octanesulfonate, bis(4-trifluoromethylphenyl)iodonium n-dodecylbenzenesulfonate, bis(4-trifluoromethylphenyl)iodonium p-toluenesulfonate, bis(4-trifluoromethylphenyl)iodonium benzenesulfonate, bis(4-trifluoromethylphenyl)iodonium 10-camphorsulfonate, bis(4-trifluoromethylphenyl) iodonium n-octanesulfonate, bis(4-trifluoromethylphenyl) iodonium 4-trifluoromethylbenzensulfonate, and bis(4-trifluoromethylphenyl)iodonium perfluorobenzenesulfonate can be given.

Among these, triphenylsulfonium trifluoromethanesulfonate, triphenylsulfonium nonafluoro-n-butanesulfonate, triphenylsulfonium 10-camphorsulfonate, (4-hydroxyphenyl)diphenylsulfonium trifluoromethanesulfonate, (4-hydroxyphenyl)diphenylsulfonium nonafluoro-n-butanesulfonate, tris(4-methoxyphenyl)sulfonium trifluoromethanesulfonate, tris(4-methoxyphenyl)sulfonium nonafluoro-n-butanesulfonate, (4-fluorophenyl)diphenylsulfonium trifluoromethanesulfonate, (4-fluorophenyl)diphenylsulfonium nonafluoro-n-butanesulfonate, 2,4,6-trimethylphenyldiphenylsulfonium trifluoromethanesulfonate, 2,4,6-trimethylphenyldiphenylsulfonium 2,4-difluorobenzenesulfonate, 2,4,6-trimethylphenyldiphenylsulfonium 4-trifluoromethylbenzensulfonate,
diphenyliodonium trifluoromethanesulfonate, diphenyliodonium nonafluoro-n-butanesulfonate, diphenyliodonium 10-camphorsulfonate, bis(4-t-butylphenyl)iodonium trifluoromethanesulfonate, bis(4-t-butylphenyl)iodonium nonafluoro-n-butanesulfonate, bis(4-t-butylphenyl)iodonium 10-camphorsulfonate, (4-fluorophenyl)phenyliodonium trifluoromethanesulfonate, (4-fluorophenyl)phenyliodonium nonafluoro-n-butanesulfonate, (4-fluorophenyl)phenyliodonium 10-camphorsulfonate, bis(4-fluorophenyl)iodonium trifluoromethanesulfonate, bis(4-fluorophenyl)iodonium nonafluoro-n-butanesulfonate, bis(4-fluorophenyl)iodonium 10-camphorsulfonate, and tris(4-trifluoromethylphenyl)sulfonium trifluoromethanesulfonate are preferable. These compounds may be used either individually or in a combination of two or more.

As specific examples of the diazomethane compounds, bis(trifluoromethanesulfonyl)diazomethane, bis(cyclohexylsulfonyl)diazomethane, bis(3,3-dimethyl-1,5-dioxaspiro[5.5]dodecane-8-sulfonyl)diazomethane, bis(1,4-dioxaspiro[4.5]decane-7-sulfonyl)diazomethane, bis(t-butylsulfonyl)diazomethane, and the like can be given.

Among these compounds, bis(cyclohexylsulfonyl)diazomethane, bis(3,3-dimethyl-1,5-dioxaspiro[5.5]dodecane-8-sulfonyl)diazomethane, and bis(1,4-dioxaspiro[4.5]decane-7-sulfonyl)diazomethane are preferable. These diazomethane compounds may be used either individually or in a combination of two or more.

Specific examples of sulfonimide compounds include N-(trifluoromethylsulfonyloxy)bicyclo[2.2.1]hept-5-ene-2,3-dicarboxyimide, N-(trifluoromethylsulfonyloxy)-7-oxabicyclo[2.2.1]hept-5-ene-2,3-dicarboxyimide, N-(trifluoromethylsulfonyloxy)bicyclo[2.2.1]heptan-5,6-oxy-2,3-dicarboxyimide; N-(10-camphorsulfonyloxy)succinimide, N-(10-camphorsulfonyloxy)phthalimide, N-(10-camphorsulfonyloxy)-7-oxabicyclo[2.2.1]hept-5-ene-2,3-dicarboxyimide, N-(10-camphorsulfonyloxy)bicyclo[2.2.1]heptan-5,6-oxy-2,3-dicarboxyimide, N-(10-camphorsulfonyloxy)naphthylimide, N-[(5-methyl-5-carboxymethylbicyclo[2.2.1]heptan-2-yl)sulfonyloxy]succinimide;
N-(n-octylsulfonyloxy)bicyclo[2.2.1]hept-5-ene-2,3-dicarboxyimide, N-(n-octylsulfonyloxy)bicyclo[2.2.1]heptane-5,6-oxy-2,3-dicarboxyimide, N-(perfluorophenylsulfonyloxy)bicyclo[2.2.1]hept-5-ene-2,3-dicarboxyimide, N-(perfluorophenylsulfonyloxy)-7-oxabicyclo[2.2.1]kept-5-ene-2,3-dicarboxyimide, N-(perfluorophenylsulfonyloxy)bicyclo[2.2.1]heptan-5,6-oxy-2,3-dicarboxyimide, N-(nonafluoro-n-butylsulfonyloxy)bicyclo[2.2.1]hept-5-ene-2,3-dicarboxyimide, N-(nonafluoro-n-butylsulfonyloxy)-7-oxabicyclo[2.2.1]hept-5-ene-2,3-dicarboxyimide, N-(nonafluoro-n-butylsulfonyloxy)bicyclo[2.2.1]heptan-5,6-oxy-2,3-dicarboxyimide;
N-(perfluoro-n-octylsulfonyloxy)bicyclo[2.2.1]hept-5-ene-2,3-dicarboxyimide, N-(perfluoro-n-octylsulfonyloxy)-7-oxabicyclo[2.2.1]hept-5-ene-2,3-dicarboxyimide, and N-(perfluoro-n-octylsulfonyloxy)bicyclo[2.2.1]heptan-5,6-oxy-2,3-dicarboxyimide.

Among these, N-(trifluoromethylsulfonyloxy)bicyclo[2.2.1]hept-5-ene-2,3-dicarboxyimide, N-(10-camphorsulfonyloxy)succinimide, and N-[(5-methyl-5-carboxymethylbicyclo[2.2.1]heptan-2-yl)sulfonyloxy]succinimide are preferable. These succinimide compounds may be used either individually or in a combination of two or more.

The radiation-sensitive acid generator (b) is added to the composition in an amount of preferably 0.1 to 30 parts by mass, more preferably 0.1 to 20 parts by mass, and particularly preferably 0.5 to 20 parts by mass for 100 parts by mass of the compound (a). If the amount of the radiation-sensitive acid generator (b) is less than 0.1 part by mass, sensitivity and developability may be impaired. If more than 30 parts by mass, transparency to radioactive rays, the pattern shape, heat resistance, and the like may be impaired.

[2-2] (c) Acid Diffusion Controller

It is desirable that the radiation-sensitive composition of the present invention further include an acid diffusion controller (c). The acid diffusion controller (c) is a component which controls diffusion of an acid generated from the radiation-sensitive acid generator (b) upon exposure in the resist film and suppresses undesired chemical reactions in the unexposed area. The addition of such an acid diffusion controller (c) improves storage stability of the resulting radiation-sensitive composition and resolution of the formed resist film. Moreover, the addition of the acid diffusion controller prevents the line width of the resist pattern from changing due to changes in the post-exposure delay (PED) which is a period of time between the completion of exposure and the post exposure heat treatment, whereby a radiation-sensitive composition with remarkably superior process stability can be obtained.

Nitrogen-containing organic compounds or photosensitive basic compounds are preferable as the acid diffusion controller (c). As examples of the nitrogen-containing organic compound, compounds shown by the following formula (7) (hereinafter called "nitrogen-containing compounds (i)"), compounds having two nitrogen atoms in the molecule (hereinafter called "nitrogen-containing compounds (ii)"), polyamino compounds or polymers having three or more nitrogen atoms (hereinafter collectively called "nitrogen-containing compounds (iii)"), amide group-containing compounds, urea compounds, nitrogen-containing heterocyclic compounds, and the like can be given.

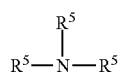
(7)

wherein $R^5$ individually represent a hydrogen atom, a substituted or unsubstituted, linear, branched, or cyclic alkyl group, a substituted or unsubstituted aryl group, or a substituted or unsubstituted aralkyl group.

As examples of the nitrogen-containing compound (i), mono(cyclo)alkylamines such as n-hexylamine, n-heptylamine, n-octylamine, n-nonylamine, n-decylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, cyclohexylmethylamine, and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, cyclohexyldimethylamine, methyldicyclohexylamine, and tricyclohexylamine; and substitute alkylamines such as triethanolamine; and aromatic amines such as aniline, N-methylaniline, N,N-dimethylaniline, 2-methylaniline, 3-methylaniline, 4-methylaniline, 4-nitroaniline, diphenylamine, triphenylamine, naphthylamine, 2,4,6-tri-tert-butyl-N-methylaniline, N-phenyldiethanolamine, and 2,6-diisopropylaniline are preferable.

Examples of the preferable nitrogen-containing compounds (ii) include ethylenediamine, N,N,N',N'-tetramethylethylenediamine, tetramethylenediamine, hexamethylenediamine, 4,4'-diaminodiphenylmethane, 4,4'-diamino diphenyl ether, 4,4'-diaminobenzophenone, 4,4'-diaminodiphenylamine, 2,2'-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, 1,3-bis[1-(4-aminophenyl)-1-methylethyl]benzene, bis(2-dimethylaminoethyl)ether, bis (2-diethylaminoethyl) ether,1-(2-hydroxyethyl)-2-imidazolizinone, 2-quinoxalinol, N,N,N',N'-tetrakis(2-hydroxypropyl)ethylenediamine, and N,N,N',N'',N''-pentamethyldiethylenetriamine.

As examples of the nitrogen-containing compound (iii), polyethyleneimine, polyallylamine, and a polymer of 2-dimethylaminoethylacrylamide are preferable.

As examples of the amide group-containing compound, N-t-butoxycarbonyl group-containing amino compounds such as N-t-butoxycarbonyl-di-n-octylamine, N-t-butoxycarbonyl-di-n-nonylamine, N-t-butoxycarbonyl-di-n-decylamine, N-t-butoxycarbonyl dicyclohexylamine, N-t-butoxycarbonyl-1-adamantylamine, N-t-butoxycarbonyl-2-adamantylamine, N-t-butoxycarbonyl-N-methyl-1-adamantylamine, (S)-(−)-1-(t-butoxycarbonyl)-2-pyrrolidinemethanol, (R)-(+)-1-(t-butoxycarbonyl)-2-pyrrolidinemethanol, N-t-butoxycarbonyl-4-hydroxypiperidine, N-t-butoxycarbonylpyrrolidine, N-t-butoxycarbonylpiperazine, N,N-di-t-butoxycarbonyl-1-adamantylamine, N,N-di-t-butoxycarbonyl-N-methyl-1-adamantylamine, N-t-butoxycarbonyl-4,4'-diaminodiphenylmethane, N,N'-di-t-butoxycarbonylhexamethylenediamine, N,N,N'N'-tetra-t-butoxycarbonylhexamethylenediamine, N,N'-di-t-butoxycarbonyl-1,7-diaminoheptane, N,N'-di-t-butoxycarbonyl-1,8-diaminooctane, N,N'-di-t-butoxycarbonyl-1,9-diaminononane, N,N'-di-t-butoxycarbonyl-1,10-diaminodecane, N,N'-di-t-butoxycarbonyl-1,12-diaminododecane, N,N'-di-t-butoxycarbonyl-4,4'-diaminodiphenylmethane, N-t-butoxycarbonylbenzimidazole, N-t-butoxycarbonyl-2-methylbenzimidazole, and N-t-butoxycarbonyl-2-phenylbenzimidazole can be given. In addition these compounds, formamide, N-methylformamide, N,N-dimethylformamide, acetamide, N-methylacetamide, N,N-dimethylacetamide, propioneamide, benzamide, pyrrolidone, N-methylpyrrolidone, N-acetyl-1-adamantylamine, tris(2-hydroxyethyl)isocyanurate, and the like are preferable.

As examples of the preferable urea compounds, urea, methylurea, 1,1-dimethylurea, 1,3-dimethylurea, 1,1,3,3-tetramethylurea, 1,3-diphenylurea, and tri-n-butylthiourea can be given.

Examples of the nitrogen-containing heterocyclic compounds include imidazoles such as imidazole, 4-methylimidazole, 4-methyl-2-phenylimidazole, benzimidazole, 2-phenylbenzimidazole, 1-benzyl-2-methylimidazole, and 1-benzyl-2-methyl-1H-imidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinamide, quinoline, 4-hydroxyquinoline, 8-oxyquinoline, acridine, and 2,2':6',2''-terpyridine; piperazines such as piperazine, 1-(2'-hydroxyethyl)piperazine; pyrazine, pyrazole, pyridazine, quinoxaline, purine, pyrrolidine, piperidine, piperidine ethanol, 3-piperidino-1,2-propanediol, morpholine, 4-methylmorpholine, 1-(4-morpholinyl)ethanol, 4-acetylmorpholine, 3-(N-morpholino)-1,2-propanediol, 1,4-dimethylpiperazine, 1,4-diazabicyclo[2.2.2]octane; and the like.

The photosensitive basic compound is a component of which the exposed area is efficiently decomposed into corresponding neutral fragments and the unexposed area remains as it is without being decomposed. Since such a photosensitive basic compound can effectively utilize the acid generated in the exposed area, the compound can improve sensitivity more effectively as compared with a non-photosensitive basic compound.

There are no specific limitations to the type of the photosensitive basic compound inasmuch as the compound has the above properties. For example, a compound shown by the following formula (8-1) and a compound shown by the following formula (8-2) can be suitably used.

(8-1)

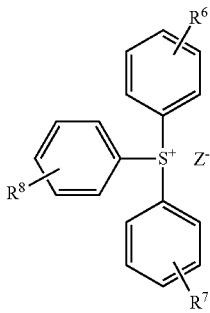

(8-2)

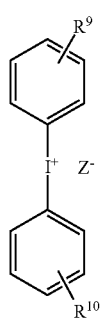

wherein, $R^6$ to $R^{10}$ individually represent a hydrogen atom, a halogen atom, a substituted or unsubstituted alkyl group having 1 to 10 carbon atoms, or a substituted or unsubstituted alicyclic hydrocarbon group and $Z^-$ is $OH^-$, $R^{11}OH^-$, or $R^{11}COO^-$, wherein $R^{11}$ represents a monovalent organic group.

As examples of the substituted or unsubstituted alkyl group having 1 to 10 carbon atoms represented by $R^6$ to $R^{10}$, a methyl group, an ethyl group, an n-butyl group, a t-butyl group, a trifluoromethyl group, a fluorine atom, a methoxy group, a t-butoxy group, and a t-butoxycarbonylmethyloxy group can be given. $R^6$ to $R^{10}$ are preferably hydrogen atoms or t-butyl groups.

As examples of the monovalent organic group represented by $R^{11}$, a substituted or unsubstituted alkyl group and a substituted or unsubstituted aryl group can be given.

As $Z^-$, $OH^-$, $CH_3COO^-$, and the groups shown by the following formulas are preferable.

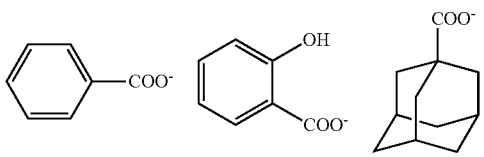

As specific examples of the photosensitive basic compound, a triphenylsulfonium compound (compound shown by the above formula (8-1)) in which the anion moiety ($Z^-$) is $OH^-$ or $CH_3COO^-$, or compounds shown by the following formulas can be given.

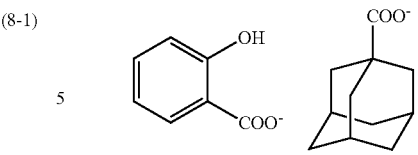

These acid diffusion controllers (c) may be used either individually or in a combination of two or more.

The acid diffusion controller (c) is added to the composition in an amount of preferably 15 parts by mass or less, more preferably 0.001 to 10 parts by mass, and particularly preferably 0.005 to 5 parts by mass for 100 parts by mass of the compound (a). If the amount of the acid diffusion controller (c) exceeds 15 parts by mass, sensitivity of the resulting resist film and developability of the exposed area may be poor. If the amount of the acid diffusion controller (c) is less than 0.001 part by mass, the pattern shape or dimensional accuracy as a resist may decrease depending on the process conditions.

[2-3] Other Components

It is desirable that the radiation-sensitive composition of the present invention include the above-mentioned compound (a), radiation-sensitive acid generator (b), and acid diffusion controller (c) dissolved in a solvent. That is, it is desirable that the composition further include a solvent as another component. Various other additives such as surfactants, sensitizers, aliphatic additives, and the like can be optionally added to the radiation-sensitive composition of the present invention.

As the solvent, at least one solvent selected from the group consisting of linear or branched ketones, cyclic ketones, propylene glycol monoalkyl ether acetates, alkyl 2-hydroxypropionates, alkyl 3-alkoxypropionates, and γ-butyrolactone (hereinafter referred to as "solvent 1") is preferable.

When used, the radiation-sensitive composition of the present invention has a total solid content of preferably 1 to 50 mass %, more preferably 1 to 25 mass %, and particularly preferably 1 to 5 mass %. The radiation-sensitive composition of the present invention can be prepared by homogeneously dissolving the compound (a), the radiation-sensitive acid generator (b), the acid diffusion controller (c), and the other optional components in a solvent so as to obtain a total solid content in the above range. The composition thus prepared is preferably filtered through a filter with a pore size of about 0.2 μm, for example.

The surfactant used as one of the other components is a component exhibiting functions of improving applicability, striation, developability, and the like. As examples of the surfactant, nonionic surfactants such as polyoxyethylene lauryl ether, polyoxyethylene stearyl ether, polyoxyethylene oleyl ether, polyoxyethylene n-octyl phenyl ether, polyoxyethylene n-nonyl phenyl ether, polyethylene glycol dilaurate, and polyethylene glycol distearate; and commercially available products such as "KP341" (manufactured by Shin-Etsu Chemical Co., Ltd.), "POLYFLOW No. 75" and "POLYFLOW No. 95" (manufactured by Kyoeisha Chemical Co., Ltd.), "FTOP EF301", "FTOP EF303", and "FTOP EF352" (manufactured by Tohkem Products Corp.), "MEGAFAC F171" and "MEGAFAC F173" (manufactured by Dainippon Ink and Chemicals, Inc.), "Fluorad FC430" and "Fluorad FC431" (manufactured by Sumitomo 3M Ltd.), "Asahi Guard AG710" and "Surflon S-382", "Surflon SC-101", "Surflon SC-102", "Surflon SC-103", "Surflon SC-104", "Surflon SC-105", and "Surflon SC-106" (manufactured by Asahi Glass Co., Ltd.) can be given.

These surfactants may be used either individually or in a combination of two or more. The amount of the surfactant is usually 0.001 to 2 parts by mass per 100 parts by mass of the compound (a).

The sensitizers absorb radiation energy and transmit the energy to the radiation-sensitive acid generator (b), thereby increasing the amount of the acid generated upon exposure. The sensitizers improve the apparent sensitivity of the radiation-sensitive composition. As examples of the sensitizer, carbazoles, acetophenones, benzophenones, naphthalenes, phenols, biacetyl, eosine, rose bengal, pyrenes, anthracenes, phenothiazines, and the like can be given. These sensitizers may be used either individually or in a combination of two or more. The amount of the sensitizer is preferably 0.1 to 10 parts by mass per 100 parts by mass of the compound (a).

Addition of a dye or a pigment visualizes a latent image in the exposed area, thereby decreasing effects of halation during exposure. Use of an adhesion improver improves adhesion of the resist film to the substrates.

Alicyclic additives having an acid-labile group and alicyclic additives having no acid-labile group may be added to the radiation-sensitive composition of the present invention. The alicyclic additives having an acid-labile group and alicyclic additives having no acid-labile group further improve dry etching resistance, pattern shape, and adhesion to the substrate.

As examples of the alicyclic additives, adamantane derivatives such as 1-adamantane carboxylate, 2-adamantanon, t-butyl-1-adamantane carboxylate, t-butoxycarbonylmethyl-1-adamantane carboxylate, α-butyrolactone-1-adamantane carboxylate, di-t-butyl-1,3-adamantanedicarboxylate, t-butyl-1-adamantane acetate, t-butoxycarbonylmethyl-1-adamantane acetate, di-t-butyl-1,3-adamantane diacetate, and 2,5-dimethyl-2,5-di(adamantylcarbonyloxy)hexane, deoxycholic acid esters such as t-butyl deoxycholate, t-butoxycarbonylmethyl deoxycholate, 2-ethoxyethyl deoxycholate, 2-cyclohexyloxyethyl deoxycholate, 3-oxocyclohexyl deoxycholate, tetrahydropyranyl deoxycholate, and mevalonolactone deoxycholate;

lithocholates such as t-butyl lithocholate, t-butoxycarbonylmethyl lithocholate, 2-ethoxyethyl lithocholate, 2-cyclohexyloxyethyl lithocholate, 3-oxocyclohexyl lithocholate, tetrahydropyranyl lithocholate, and mevalonolactone lithocholate; alkyl carboxylates such as dimethyl adipate, diethyl adipate, dipropyl adipate, di-n-butyl adipate, and di-t-butyl adipate; 3-[2-hydroxy-2,2-bis(trifluoromethyl)ethyl]tetracyclo[4.4.0.1$^{2,5}$.1$^{7,10}$]dodecane, and the like can be given.

These alicyclic additives may be used either individually or in combination. The amount of the alicyclic additive is usually 0.5 to 20 parts by mass per 100 parts by mass of the compound (a). If the amount of the alicyclic additive exceeds 20 parts by mass, heat resistance of the resulting resist film may be poor.

As other additives, low molecular weight alkali solubility controllers containing an alkali-soluble resin and/or an acid-labile protecting group, halation inhibitors, preservation stabilizers, antifoaming agents, and the like can be given.

[3] Resist Pattern Forming Method

The radiation-sensitive composition of the present invention is particularly useful as a chemically-amplified resist. In the chemically-amplified resist, an acid-labile group in the compound (a) dissociates by the action of an acid generated from the radiation-sensitive acid generator (b) upon exposure, thereby producing alkali soluble sites. As a result, solubility of the exposed part of the resist film in an alkaline developer increases, whereby the exposed part is dissolved in the alkaline developer and removed. A positive-tone resist pattern can thus be obtained.

A resist pattern is formed from the radiation-sensitive composition of the present invention by applying the composition solution to a substrate such as a silicon wafer or a wafer coated with aluminum using an appropriate application method such as rotational coating, cast coating, and roll coating to form a resist film. The resist film is then optionally pre-baked (hereinafter called "PB") and exposed to form a predetermined resist pattern. As radiation which can be used for the exposure, deep ultraviolet rays such as a KrF excimer laser (wavelength: 248 nm), EUV (extreme ultraviolet rays, wavelength: 13 nm), X-rays such as synchrotron radiation, charged particle rays such as electron beams, and the like can be suitably selected. The exposure conditions such as an amount of exposure are appropriately determined according to the composition of the radiation-sensitive composition, types of additives, and the like. Liquid immersion lithography may be used.

In the present invention, it is preferable to perform post-exposure bake (hereinafter called "PEB") after exposure. PEB ensures smooth dissociation of the acid-labile group froth the compound (a). The PEB temperature varies depending on the composition of the radiation-sensitive composition, but is preferably 30 to 200° C., and more preferably 50 to 170° C.

In order to bring out the potential capability of the radiation-sensitive composition to the maximum extent, an organic or inorganic antireflection film may be formed on the substrate as disclosed in JP-B-6-12452, for example. In addition, a protective film may be provided on the resist film in order to prevent an adverse effect of basic impurities and the like that are present in the environmental atmosphere using a method described in, for example, JP-A-5-188598. These techniques may be used in combination.

The exposed resist film is then developed to form a specific resist pattern. As a developer, an aqueous alkaline solution prepared by dissolving at least one alkaline compound selected from sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, 1,5-diazabicyclo-[4.3.0]-5-nonene, and the like is preferably used.

The concentration of the aqueous alkaline solution is preferably 10 mass % or less. If the concentration of the aqueous alkaline solution exceeds 10 mass %, an unexposed area may also be dissolved in the developer. The pH of the developer is preferably 8 to 14, and more preferably 9 to 14.

Organic solvents or the like may be added to the developer containing the aqueous alkaline solution. As examples of the organic solvent, ketones such as acetone, methyl ethyl ketone, methyl i-butyl ketone, cyclopentanone, cyclohexanone, 3-methylcyclopentanone, and 2,6-dimethylcyclohexanone; alcohols such as methylalcohol, ethylalcohol, n-propylalcohol, i-propylalcohol, n-butylalcohol, t-butylalcohol, cyclopentanol, cyclohexanol, 1,4-hexanediol, and 1,4-hexanedimethylol; ethers such as tetrahydrofuran and dioxane; esters such as ethyl acetate, n-butyl acetate, and i-amyl acetate; aromatic hydrocarbons such as toluene and xylene; phenol; acetonylacetone; and dimethylformamide can be given. These organic solvents may be used either individually or in a combination of two or more.

The amount of the organic solvent to be used is preferably 100 parts by volume or less for 100 parts by volume of the aqueous alkaline solution. An amount of the organic solvent exceeding 100 parts by volume may decrease developability, giving rise to a larger undeveloped portion in the exposed area. In addition, an appropriate amount of a surfactant or the like may be added to the developer of an aqueous alkaline solution. After development using the aqueous alkaline solution developer, the resist film may be washed with water and dried.

EXAMPLES

The present invention is described below in detail based on examples. However, the present invention is not limited to the following examples. In the examples, "part" refers to "parts by mass" and "%" refers to "mass %" unless otherwise indicated.

The following compounds (A-1) and (A-2) were synthesized as compounds shown by the formula (1) (Compound (a)) and the following compounds (A-3) and (A-4) were synthesized for comparison.

Example 1

Compound (A-1)

22.0 g (200 mmol) of resorcinol was added to and dissolved in 45 ml of ethanol and 15 ml of hydrochloric acid was added. The solution was cooled with ice to 5° C. while stirring and 10.0 g (50 mmol) of a 50% aqueous solution of glutaraldehyde was slowly added dropwise. After the addition, the mixture was heated at 80° C. for 48 hours to obtain a cloudy yellow suspension. The suspension was poured into methanol, and the resulting precipitate was collected by filtration. The precipitate was washed three times with methanol. The washed precipitate was dried under reduced pressure at room temperature for 24 hours to obtain a powdery light yellow solid (S) (11.2 g (yield: 79%)).

The structure of the resulting light yellow solid (S) was identified using an MALDI-TOF-MS (Model No. SHIMAZU/KRATOS matrix support laser ionization flight time-type mass spectroscope, KOMPACT MALDI IV tDE, manufactured by Shimadzu Corp.), an IR (Model No. FT-IR 420-type, manufactured by Jasco Corp.), and a $^1$H-NMR (Model No. JNM-ECA-500-type manufactured by JEOL Ltd.). The results are shown below.

MALDI-TOF-MS: Production of only a compound having a molecular weight of 1705 was confirmed.

IR (film method): (cm$^{-1}$)

3406 ($v_{OH}$); 2931 ($v_{C-H}$); 1621, 1505, 1436 ($v_{C=C}$ (aromatic))

$_1$H-NMR (400 MHz, solvent DMSO-d$_6$, internal standard TMS): δ (ppm)=0.80-2.20 (b, 12.0H), 3.98-4.22 (m, 4.0H), 6.09-7.42 (m, 8.0H), 8.65-9.56 (m, 8.0H)

1.2 g of tetrabutylammonium bromide was added to 5.1 g of the resulting light yellow solid. After further addition of 30 g of 1-methyl-2-pyrrolidone, the mixture was stirred at 70° C. for one hour to dissolve the light yellow solid. After dissolution, 6.0 g of potassium carbonate was added and the mixture was stirred at 70° C. for one hour. Then, a solution of 8.4 g of t-butyl bromoacetate dissolved in 10 g of 1-methyl-2-pyrrolidone was slowly added and the mixture was stirred at 60° C. for six hours. After the reaction, the reaction mixture was cooled to room temperature and poured into 300 ml of a 3% oxalic acid aqueous solution to precipitate a solid. The resulting solid was dissolved in methylene chloride and the solution was washed three times with 100 ml of a 3% oxalic acid aqueous solution and two times with 100 ml of water. After discharging the aqueous layer, the organic layer was dried using magnesium sulfate and purified by a silica gel column using a 1:4 (volume ratio) mixture of hexane and ethyl acetate as eluant to obtain 3.2 g of a Compound (A-1).

As a result of $^1$H-NMR analysis, the Compound (A-1) was found to be a compound of the formula (2) in which 50 mol % of R was a group shown by the following formula (R-1) (t-butyl-oxycarbonylmethyl group), with the remaining R being hydrogen atoms.

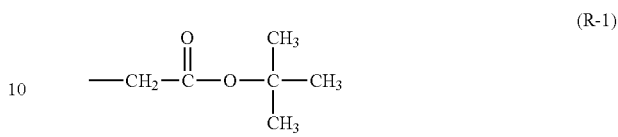

(R-1)

The results of $^1$H-NMR analysis were as follows.
$^1$H-NMR (400 MHz, solvent DMSO-d$_6$, internal standard TMS): δ (ppm)=0.82-2.40 (m, 48.0H), 3.80-5.00 (m, 12.0H), 6.08-7.41 (m, 8.0H), 8.60-9.55 (m, 4.0H)

Example 2

Compound (A-2)

After the addition of 1.6 g of tetrabutylammonium bromide and 24 ml of dehydrated pyridine to 6.8 g of the light yellow solid (S) obtained in Example 1, the mixture was stirred for one hour. Then, 12.6 g of di-t-butyldicarbonate was gradually added and the mixture was stirred at room temperature for 48 hours. After the reaction, the reaction mixture was cooled to room temperature and poured into 300 ml of a 3% oxalic acid aqueous solution to precipitate a solid. The resulting solid was dissolved in methylene chloride and the solution was washed three times with 100 ml of a 3% oxalic acid aqueous solution and two times with 100 ml of water. After discharging the aqueous layer, the organic layer was dried using magnesium sulfate and purified by a silica gel column using a 1:1 (volume ratio) mixture of hexane and ethyl acetate as eluant to obtain 5.0 g of a Compound (A-2).

As a result of $^1$H-NMR analysis, the Compound (A-2) was found to be a compound of the formula (2) in which 50 mol % of R was a group shown by the following formula (R-2) (t-butoxycarbonyl group), with the remaining R being hydrogen atoms.

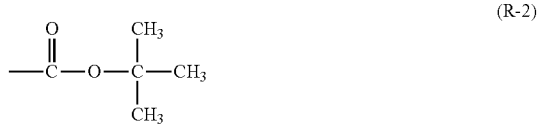

(R-2)

Example 3

100 parts of the Compound (A-1), 9 parts of triphenylsulfonium trifluoromethanesulfonate (shown in Table 1 as "B-1") as a radiation-sensitive acid generator (b), 1.5 parts of tri-n-octylamine (shown in Table 1 as "C-1") as an acid diffusion controller (c), 600 parts of ethyl lactate (shown in Table 1 as "D-1") as a solvent, and 1500 parts of propylene glycol monomethyl ether acetate (shown in Table 1 as "D-3") were mixed. The mixture was filtered through a membrane filter having a pore diameter of 200 nm to obtain a composition solution (radiation-sensitive composition). The amount of each component is shown in Table 1.

Each composition solution was then applied onto a silicon wafer using a spin coater and pre-baked for 90 seconds at 130° C. in a clean track (ACT-8 manufactured by Tokyo Electron, Ltd.) to form a resist (radiation-sensitive composition) film with a thickness of 70 nm. The resist film was irradiated with an electron beam using a simplified electron beam writer (HL800D manufactured by Hitachi, Ltd., output: 50 KeV, current density: 5.0 A/cm$^2$). After exposure to electron beams, the resist film was baked (PEB) at 130° C. for 90 seconds. A resist pattern was obtained by developing the resist at 23° C. for 1 minute by a paddle method using a 2.38% tetramethylammonium hydroxide aqueous solution, followed by washing with purified water and drying. Evaluation of resists was carried out as follows.

(1) Sensitivity (L/S)

A resist pattern was formed by irradiating the resist film formed on a silicon wafer, immediately followed by baking (PEB), alkali development, washing with water, and drying. In this instance, an exposure amount required for forming a 1:1 line-and-space pattern (1L1S) with a line width of 150 nm was regarded as an optimal exposure dose, which was taken as sensitivity.

(2) Resolution (L/S)

In the line-and-space (1L1S) pattern, the minimum line width (nm) of line pattern resolved by the optimum exposure dose was taken as the resolution.

(3) Pattern Shape

In a line-and-space pattern (1L1S) with a design line width of 0.15 μm resolved at an optimum dose, the relationship between the upper side dimension A (nm) and the lower side dimension B (nm) was determined. When a formula $0.85 \leq (A/B) \leq 1.2$ was satisfied, the pattern shape was evaluated as "Good", when a formula $(A/B)<0.85$ was satisfied, the pattern shape was evaluated as "Forward tapered shape", and when a formula $1.2<(A/B)$ was satisfied, the pattern shape was evaluated as "Inverse tapered shape".

As a result of the evaluation of Examples, the sensitivity was 31.0 μC/cm², the resolution was 70 nm, and the pattern shape was "Good". Evaluation results are shown in Table 3.

Examples 4 to 24

The composition solutions (radiation-sensitive compositions) were prepared in the same manner as in Example 3, except for preparing homogenous solutions using the components shown in Table 1 in amounts shown in Table 1 and treating the resulting composition solutions under the conditions shown in Table 3. Resist patterns were formed using the resulting radiation-sensitive compositions to evaluate the performance of the resist films. The evaluation results are shown in Table 3.

Comparative Example 1

0.19 g of tetrabutylammonium bromide was added to 0.85 g of the light yellow solid (S) obtained in Example 1. After further addition of 3 g of 1-methyl-2-pyrrolidone, the mixture was stirred at 70° C. for one hour to dissolve the solid (S). After dissolution, 5.86 g of potassium carbonate was added and the mixture was stirred at 70° C. for one hour. Then, a solution of 3.51 g of t-butyl bromoacetate dissolved in 1 g of 1-methyl-2-pyrrolidone was slowly added and the mixture was stirred at 80° C. for 48 hours. The reaction mixture was cooled to room temperature and poured into 50 ml of a 3% oxalic acid aqueous solution to precipitate a solid. The resulting solid was dissolved in methylene chloride and the solution was washed three times with 50 ml of a 3% oxalic acid aqueous solution and two times with 50 ml of water. After discharging the aqueous layer, the organic layer was dried using magnesium sulfate and, after separating the magnesium sulfate, purified by silica gel column chromatography using a 1:4 (volume ratio) mixture of hexane and ethyl acetate as eluant to obtain 0.36 g of a Compound (A-3).

As a result of $^1$H-NMR analysis, the Compound (A-3) was found to be a compound shown by the following formula (A-3) in which all R was a group shown by the following formula (R-3) (tert-butoxycarbonylmethyl group).

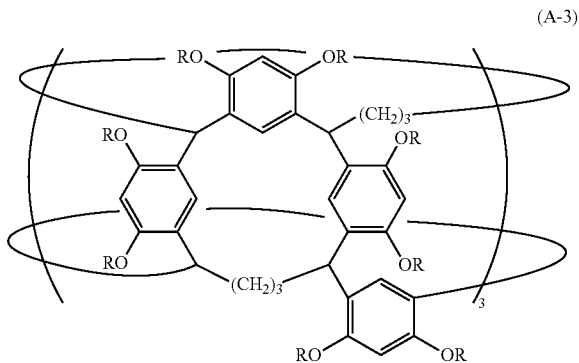

(A-3)

TABLE 1

| Example | Compound (a) Type | Compound (a) Amount (Parts) | Radiation-sensitive acid generator (b) Type | Radiation-sensitive acid generator (b) Amount (Parts) | Type | Amount (Parts) | Acid diffusion controller (c) Type | Acid diffusion controller (c) Amount (Parts) | Type | Amount (Parts) | Solvent Type | Solvent Amount (Parts) | Type | Amount (Parts) |
|---|---|---|---|---|---|---|---|---|---|---|---|---|---|---|
| Example 3  | A-1 | 100 | B-1 | 9 | —   | — | C-1 | 1.5 | —   | —   | D-1 | 600 | D-3 | 1500 |
| Example 4  | A-1 | 100 | B-2 | 9 | —   | — | C-3 | 1.5 | —   | —   | D-1 | 600 | D-3 | 1500 |
| Example 5  | A-1 | 100 | B-3 | 9 | —   | — | C-1 | 1.5 | C-4 | 0.1 | D-1 | 600 | D-3 | 1500 |
| Example 6  | A-1 | 100 | B-6 | 9 | —   | — | C-1 | 1.5 | —   | —   | D-1 | 600 | D-2 | 1500 |
| Example 7  | A-1 | 100 | B-7 | 9 | —   | — | C-1 | 1.5 | —   | —   | D-1 | 600 | D-3 | 1500 |
| Example 8  | A-1 | 100 | B-1 | 9 | B-6 | 3 | C-1 | 1.5 | —   | —   | D-1 | 600 | D-2 | 1500 |
| Example 9  | A-1 | 100 | B-1 | 9 | B-7 | 3 | C-1 | 1.5 | —   | —   | D-1 | 600 | D-3 | 1500 |
| Example 10 | A-1 | 100 | B-1 | 9 | —   | — | C-2 | 2.1 | —   | —   | D-1 | 600 | D-3 | 1500 |
| Example 11 | A-1 | 100 | B-1 | 9 | —   | — | C-2 | 2.1 | —   | —   | D-1 | 600 | D-3 | 1500 |
| Example 12 | A-1 | 100 | B-1 | 9 | —   | — | C-2 | 2.1 | —   | —   | D-1 | 600 | D-3 | 1500 |
| Example 13 | A-1 | 100 | B-1 | 9 | —   | — | C-5 | 1.1 | —   | —   | D-1 | 600 | D-3 | 1500 |
| Example 14 | A-1 | 100 | B-1 | 9 | —   | — | C-6 | 1.1 | —   | —   | D-1 | 600 | D-3 | 1500 |
| Example 15 | A-1 | 100 | B-1 | 9 | B-7 | 3 | C-5 | 1.1 | —   | —   | D-1 | 600 | D-3 | 1500 |
| Example 16 | A-1 | 100 | B-1 | 9 | B-7 | 3 | C-6 | 1.1 | —   | —   | D-1 | 600 | D-3 | 1500 |
| Example 17 | A-1 | 100 | B-1 | 9 | B-7 | 3 | C-2 | 2.1 | —   | —   | D-1 | 600 | D-3 | 1500 |
| Example 18 | A-2 | 100 | B-1 | 9 | —   | — | C-1 | 1.5 | —   | —   | D-1 | 600 | D-3 | 1500 |
| Example 19 | A-2 | 100 | B-1 | 9 | B-6 | 3 | C-1 | 1.5 | —   | —   | D-1 | 600 | D-2 | 1500 |
| Example 20 | A-2 | 100 | B-1 | 9 | B-7 | 3 | C-1 | 1.5 | —   | —   | D-1 | 600 | D-3 | 1500 |

-continued $$-CH_2-\overset{O}{\underset{\|}{C}}-O-\underset{\underset{CH_3}{|}}{\overset{\overset{CH_3}{|}}{C}}-CH_3 \quad (R\text{-}3)$$

Composition solutions (radiation-sensitive compositions) were prepared in the same manner as in Example 3, except for preparing homogenous solutions by mixing the Compound (A-3) and the components shown in Table 2 in amounts shown in Table 2 and treating the resulting composition solutions under the conditions shown in Table 3. Resist patterns were formed using the resulting radiation-sensitive compositions to evaluate the performance of the resist films. The evaluation results are shown in Table 3.

Comparative Example 2

After the addition of 0.19 g of tetrabutylammonium bromide and 6 ml of dehydrated pyridine to 0.85 g of the light yellow solid (S) obtained in Example 1, the mixture was stirred for one hour. 5.2 g of di-t-butyldicarbonate was gradually added and the mixture was stirred at room temperature for 48 hours. The reaction mixture was cooled to room temperature and poured into 300 ml of a 3% oxalic acid aqueous solution to precipitate a solid. The resulting solid was dissolved in methylene chloride and the solution was washed three times with 100 ml of a 3% oxalic acid aqueous solution and two times with 100 ml of water. After discharging the aqueous layer, the organic layer was dried using magnesium sulfate and purified by a silica gel column using a 1:1 (volume ratio) mixture of hexane and ethyl acetate as eluant to obtain 1.66 g of a Compound (A-4).

TABLE 2

|  | Compound (a) | | Radiation-sensitive acid generator (b) | | | | Acid diffusion controller (c) | | | | Solvent | | | |
| --- | --- | --- | --- | --- | --- | --- | --- | --- | --- | --- | --- | --- | --- | --- |
|  | Type | Amount (Parts) | Type | Amount (Parts) | Type | Amount (Parts) | Type | Amount (Parts) | Type | Amount (Parts) | Type | Amount (Parts) | Type | Amount (Parts) |
| Example 21 | A-2 | 100 | B-1 | 9 | — | — | C-2 | 2.1 | — | — | D-1 | 600 | D-3 | 1500 |
| Example 22 | A-2 | 100 | B-1 | 9 | B-7 | 3 | C-5 | 1.1 | — | — | D-1 | 600 | D-3 | 1500 |
| Example 23 | A-2 | 100 | B-1 | 9 | B-7 | 3 | C-6 | 1.1 | — | — | D-1 | 600 | D-3 | 1500 |
| Example 24 | A-2 | 100 | B-1 | 9 | B-7 | 3 | C-2 | 2.1 | — | — | D-1 | 600 | D-3 | 1500 |
| Comparative Example 1 | A-3 | 100 | B-1 | 9 | — | — | C-1 | 1.5 | — | — | D-1 | 600 | D-3 | 1500 |
| Comparative Example 2 | A-4 | 100 | B-1 | 9 | — | — | C-1 | 1.5 | — | — | D-1 | 600 | D-3 | 1500 |

TABLE 3

|  | PB Conditions | | PEB Conditions | | Sensitivity ($\mu C/cm^2$) | Resolution | Pattern shape |
| --- | --- | --- | --- | --- | --- | --- | --- |
|  | Temp. (° C.) | Time (sec) | Temp. (° C.) | Time (sec) | | | |
| Example 3 | 130 | 90 | 130 | 90 | 31.0 | 70 nm | Good |
| Example 4 | 130 | 90 | 130 | 90 | 34.0 | 80 nm | Good |
| Example 5 | 130 | 90 | 130 | 90 | 33.0 | 80 nm | Good |
| Example 6 | 130 | 90 | 120 | 90 | 32.0 | 70 nm | Good |
| Example 7 | 130 | 90 | 120 | 90 | 32.0 | 70 nm | Good |
| Example 8 | 130 | 90 | 130 | 90 | 31.0 | 70 nm | Good |
| Example 9 | 130 | 90 | 130 | 90 | 31.0 | 70 nm | Good |
| Example 10 | 130 | 90 | 130 | 90 | 32.0 | 70 nm | Good |
| Example 11 | 130 | 90 | 110 | 90 | 33.0 | 70 nm | Good |
| Example 12 | 130 | 90 | 90 | 90 | 34.0 | 70 nm | Good |
| Example 13 | 130 | 90 | 130 | 90 | 32.0 | 80 nm | Good |
| Example 14 | 130 | 90 | 130 | 90 | 32.0 | 80 nm | Good |
| Example 15 | 130 | 90 | 130 | 90 | 31.0 | 70 nm | Good |
| Example 16 | 130 | 90 | 130 | 90 | 31.0 | 70 nm | Good |
| Example 17 | 130 | 90 | 130 | 90 | 30.0 | 70 nm | Good |
| Example 18 | 90 | 90 | 90 | 90 | 35.0 | 90 nm | Good |
| Example 19 | 90 | 90 | 90 | 90 | 34.0 | 90 nm | Good |
| Example 20 | 90 | 90 | 90 | 90 | 34.0 | 90 nm | Good |
| Example 21 | 90 | 90 | 90 | 90 | 34.0 | 80 nm | Good |
| Example 22 | 90 | 90 | 90 | 90 | 33.0 | 80 nm | Good |
| Example 23 | 90 | 90 | 90 | 90 | 33.0 | 80 nm | Good |
| Example 24 | 90 | 90 | 90 | 90 | 33.0 | 80 nm | Good |
| Comparative Example 1 | 130 | 90 | 130 | 90 | 37.0 | 150 nm | Inverse tapered |
| Comparative Example 2 | 90 | 90 | 90 | 90 | 38.0 | 150 nm | Inverse tapered |

As a result of $^1$H-NMR analysis, the Compound (A-4) was found to be a compound shown by the following formula (A-4) in which all R was a group shown by the following formula (R-4) (tert-butoxycarbonyl group).

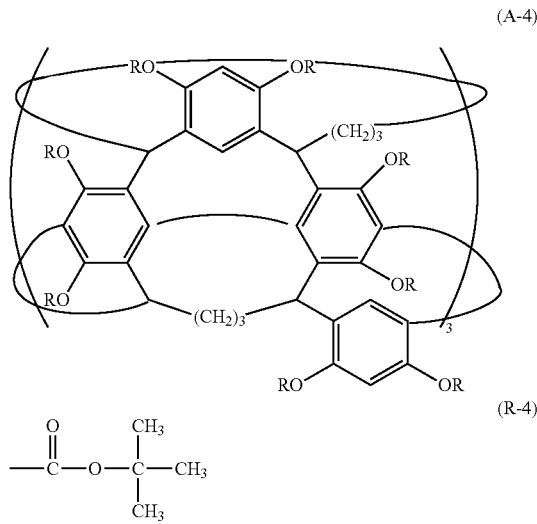

Composition solutions (radiation-sensitive compositions) were prepared in the same manner as in Example 3, except for preparing homogenous solutions by mixing the Compound (A-4) and the components shown in Table 2 in amounts shown in Table 2 and treating the resulting composition solutions under the conditions shown in Table 3. Resist patterns were formed using the resulting radiation-sensitive compositions to evaluate the performance of the resist films. The evaluation results are shown in Table 3.

Materials used in Examples 3 to 24 and Comparative Examples 1 and 2 are shown below.
(b) Radiation-Sensitive Acid Generator:
B-1: triphenylsulfonium trifluoromethanesulfonate
B-2: N-(trifluoromethylsulfonyloxy)bicyclo[2.2.1]hept-5-ene-2,3-dicarboxyimide
B-3: 2,4,6-trimethylphenyldiphenylsulfonium 4-trifluoromethylbenzensulfonate
B-6: triphenylsulfonium 1,1,2,2-tetrafluoro-2-(tetracyclo[4.4.0.1$^{2,5}$.1$^{7,10}$]dodecan-8-yl)ethanesulfonate
B-7: triphenylsulfonium 1,1-difluoro-2-(bicyclo[2.2.1]heptane-2-yl)ethanesulfonate
(c) Acid Diffusion Controller:
C-1: Tri-n-octylamine
C-2: Triphenylsulfonium salicylate
C-3: N-t-butoxycarbonyldicyclohexylamine
C-4: 4-Phenyl pyridine
C-5: (R)-(+)-1-(t-butoxycarbonyl)-2-pyrrolidinemethanol
C-6: (S)-(−)-1-(t-butoxycarbonyl)-2-pyrrolidinemethanol
Solvents:
D-1: Ethyl lactate
D-2: Ethyl 3-ethoxypropionate
D-3: Propylene glycol monomethyl ether acetate As clearly shown in Table 3, the radiation-sensitive compositions of Examples 3 to 24 which contain any one of the compounds of Examples 1 and 2 were confirmed to be able to form a chemically-amplified positive-tone resist film which effectively responds to electron beams or extreme ultraviolet rays, exhibits excellent resolution, sensitivity, and pattern shape, and can form high precision minute patterns in a stable manner using EB, EUV, and X rays, as compared with the radiation-sensitive compositions of Comparative Examples 1 and 2.

The compound of the present invention can be suitably used in the field of microfabrication represented by the manufacturing of integrated circuit elements. When the compound is used in preparing a radiation-sensitive composition, the resulting composition is suitably used as a material for forming a chemically amplified resist for the manufacture of semiconductor devices.

The radiation-sensitive composition of the present invention can be suitably used in the field of microfabrication represented by the manufacturing of integrated circuit elements. It is particularly suitable as a material for forming a chemically amplified resist film for the manufacture of semiconductor devices.

The invention claimed is:
1. A compound shown by the following formula (1),

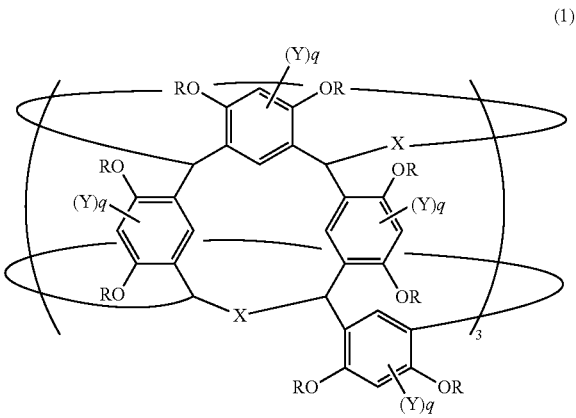

wherein R individually represent a hydrogen atom or a substituted or unsubstituted monovalent acid-labile group having a chain-like structure, X individually represent a substituted or unsubstituted alkylene group having 1 to 8 carbon atoms; Y individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxy group having 1 to 10 carbon atoms, or a substituted or unsubstituted phenoxy group, and q individually represent 0 or 1, and
wherein a content of the substituted or unsubstituted monovalent acid-labile groups each represented by R with respect to all Rs is from 10 to 50 mol %.
2. The compound according to claim 1, wherein the acid-labile group is a group shown by the following formula (2-1) or (2-2),

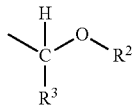
(2-2)

wherein A represents a methylene group or a divalent alkylene group having 2 to 11 carbon atoms which may be unsubstituted or substituted by a substituent which may include a hetero atom, n represents an integer from 0 to 3, and $R^1$ represents a linear or branched alkyl group having 1 to 40 carbon atoms which may be unsubstituted or substituted by a substituent which may include a hetero atom, $R^2$ represents an alkyl group having 1 to 40 carbon atoms which may be unsubstituted or substituted by a substituent which may include a hetero atom, and $R^3$ represents a hydrogen atom or an alkylene group having 1 to 5 carbon atoms.

3. The compound according to claim 2, wherein the group shown by the formula (2-1) is a group shown by the following formula (3-1) or (3-2), and the group shown by the formula (2-2) is a group shown by the following formula (4-1), (4-2), (4-3), or (4-4),

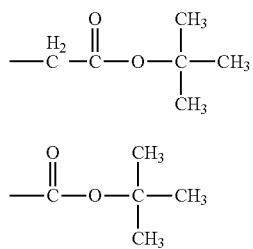
(3-1)

(3-2)

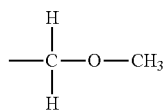
(4-1)

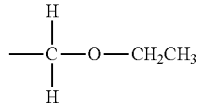
(4-2)

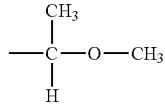
(4-3)

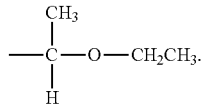
(4-4)

4. A radiation-sensitive composition comprising (a) the compound according to claim 1, and (b) a radiation-sensitive acid generator which generates an acid upon irradiation.

5. The radiation-sensitive composition according to claim 4, wherein the radiation-sensitive acid generator (b) is at least one compound selected from the group consisting of an onium salt, a diazomethane compound, and a sulfonimide compound.

6. The radiation-sensitive composition according to claim 4, further comprising (c) an acid diffusion controller.

* * * * *